United States Patent
Lin et al.

(10) Patent No.: US 10,613,622 B2
(45) Date of Patent: Apr. 7, 2020

(54) METHOD AND DEVICE FOR CONTROLLING VIRTUAL REALITY HELMETS

(71) Applicant: Beijing Xiaomi Mobile Software Co., Ltd., Beijing (CN)

(72) Inventors: Xingsheng Lin, Beijing (CN); Xuanran Wang, Beijing (CN); Zhiyong Feng, Beijing (CN)

(73) Assignee: Beijing Xiaomi Mobile Software Co., Ltd., Beijing (CN)

( * ) Notice: Subject to any disclaimer, the term of this patent is extended or adjusted under 35 U.S.C. 154(b) by 0 days.

(21) Appl. No.: 15/917,229

(22) Filed: Mar. 9, 2018

(65) Prior Publication Data
US 2018/0267600 A1    Sep. 20, 2018

(30) Foreign Application Priority Data
Mar. 14, 2017    (CN) .......................... 2017 1 0150111

(51) Int. Cl.
*G06F 3/00* (2006.01)
*G06F 3/01* (2006.01)
(Continued)

(52) U.S. Cl.
CPC ............ *G06F 3/011* (2013.01); *G02B 27/017* (2013.01); *G06F 1/163* (2013.01);
(Continued)

(58) Field of Classification Search
CPC ...................................................... G06F 3/011
(Continued)

(56) References Cited

U.S. PATENT DOCUMENTS 9,143,715 B2    9/2015   Riddell et al.
2004/0090423 A1  5/2004   Bisset
(Continued)

FOREIGN PATENT DOCUMENTS

CN    103999030 A    8/2014
CN    105031918 A    11/2015
(Continued)

OTHER PUBLICATIONS

Extended European Search Report dated Aug. 31, 2018 in Patent Application No. 18161593.1.
(Continued)

*Primary Examiner* — Andrey Belousov
(74) *Attorney, Agent, or Firm* — Oblon, McClelland, Maier & Neustadt, L.L.P.

(57) ABSTRACT

A method and device for controlling Virtual Reality (VR) helmet are provided. The method includes detecting a touch action on a touch control panel; generating a control instruction corresponding to the touch action, the touch action being a sliding operation along a predetermined direction on the touch control panel; sending the control instruction to the VR equipment; detecting attributes and arrangements of all operation objects in a current display interface; when the row number and the column number of all the arranged operation objects are both larger than 1, controlling a switching selection to be performed among the operation objects based on the attributes of the operation objects; and when the row number or the column number of all the arranged operation objects is 1, controlling the switching selection to be performed among the operation objects based on an arrangement direction of the operation objects.

11 Claims, 7 Drawing Sheets

(51) Int. Cl.
    *G06F 3/0483*     (2013.01)
    *G06F 3/0488*     (2013.01)
    *G06F 1/16*     (2006.01)
    *G06F 3/0482*     (2013.01)
    *G06F 3/0354*     (2013.01)
    *G02B 27/01*     (2006.01)
    *G06F 3/041*     (2006.01)
    *G06F 3/0481*     (2013.01)
    *G06F 3/0484*     (2013.01)
    *H04N 21/422*     (2011.01)

(52) U.S. Cl.
    CPC ........ *G06F 3/03547* (2013.01); *G06F 3/0416* (2013.01); *G06F 3/0482* (2013.01); *G06F 3/0483* (2013.01); *G06F 3/0488* (2013.01); *G06F 3/04815* (2013.01); *G06F 3/04817* (2013.01); *G06F 3/04842* (2013.01); *G06F 3/04883* (2013.01); *A61M 2205/507* (2013.01); *A63F 2300/8082* (2013.01); *H04N 21/42224* (2013.01)

(58) Field of Classification Search
    USPC .......................................... 715/863, 784, 830
    See application file for complete search history.

(56) References Cited

U.S. PATENT DOCUMENTS

| | | | |
|---|---|---|---|
| 2012/0032901 A1* | 2/2012 | Kwon | G06F 3/04883 345/173 |
| 2014/0204279 A1 | 7/2014 | Kwon | |
| 2014/0267932 A1 | 9/2014 | Riddell et al. | |
| 2015/0002434 A1 | 1/2015 | Tsukahara et al. | |
| 2015/0323988 A1 | 11/2015 | Kuehne | |
| 2016/0291687 A1* | 10/2016 | Kasahara | G06F 3/03547 |
| 2017/0134790 A1 | 5/2017 | Kwon | |
| 2017/0336882 A1 | 11/2017 | Tome et al. | |
| 2018/0005607 A1 | 1/2018 | Tsukahara et al. | |

FOREIGN PATENT DOCUMENTS

| | | |
|---|---|---|
| CN | 105210144 A | 12/2015 |
| EP | 2 799 958 A1 | 11/2014 |
| EP | 3 001 407 A1 | 3/2016 |
| WO | WO 2017/201162 A1 | 11/2017 |

OTHER PUBLICATIONS

Chinese Office Action dated Mar. 28, 2019 in Patent Application No. 201710150111.4.

\* cited by examiner

METHOD AND DEVICE FOR CONTROLLING VIRTUAL REALITY HELMETS

CROSS-REFERENCE TO RELATED APPLICATIONS

This application is filed based upon and claims priority to Chinese Patent Application Serial No. 201710150111.4, filed on Mar. 14, 2017, the entire contents of which are incorporated herein by reference.

TECHNICAL FIELD

The present disclosure generally relates to the technical field of Virtual Reality (VR), and more particularly, to a method and device for controlling a VR helmet.

BACKGROUND

Along with development of sciences and technologies, a VR technology has already appeared on the market. The VR technology is an intelligent equipment simulation system capable of creating a virtual world by generating a simulated environment by virtue of intelligent equipment. The VR technology is a simulation system for an interactive three-dimensional dynamic view and entity behavior of multi-source information fusion, and may enable a user to be immersed in the environment.

VR equipment may be a helmet, and may also be additionally provided with a handle capable of communicating with the helmet (or a mobile phone in the helmet) through a BlueTooth (BT) or Wireless Fidelity (WI-FI) technology.

In a related technology, a handle is keyed. Multiple physical keys are arranged in the handle, and when a user presses the physical keys, corresponding operation instructions may be generated, and a helmet is controlled to perform corresponding actions according to the operation instructions. However, a keying manner increases complexity of an operation of the user, and the user is usually required to press the keys many times to achieve an expected control effect.

SUMMARY

This Summary is provided to introduce a selection of aspects of the present disclosure in a simplified form that are further described below in the Detailed Description. This Summary is not intended to identify key features or essential features of the claimed subject matter, nor is it intended to be used to limit the scope of the claimed subject matter.

Aspects of the disclosure provide a method for controlling Virtual Reality (VR) equipment. The method includes detecting a touch action on a touch control panel; generating a control instruction corresponding to the touch action, the touch action being a sliding operation along a predetermined direction on the touch control panel; sending the control instruction to the VR equipment; detecting attributes and arrangements of all operation objects in a current display interface; determining a row number and a column number of all the arranged operation objects; when the row number and the column number of all the arranged operation objects are both larger than 1, controlling a switching selection to be performed among the operation objects based on the attributes of the operation objects; and when the row number or the column number of all the arranged operation objects is 1, controlling the switching selection to be performed among the operation objects based on an arrangement direction of the operation objects.

In an example, when all the operation objects comprise tag items and resource items, and the row number and the column number of all the arranged operation objects are both larger than 1, the switching selection is controlled to be performed among different tag items or among different resource items based on a corresponding relationship between the sliding operation in the predetermined direction and an attribute of an operation object.

According to an aspect, the method includes detecting a first touch action on the touch control panel; generating a first control instruction corresponding to the first touch action, the first touch action being a sliding operation along a first direction on the touch control panel, and the first control instruction being configured to control different resource items in the display interface of the VR equipment to be switched; detecting a second touch action on the touch control panel; and generating a second control instruction corresponding to the third touch action, the second touch action being a sliding operation along a second direction on the touch control panel, and the second control instruction being configured to control different tag items in the display interface of the VR equipment to be switched. The first direction is different from the second direction.

In an example, the resource items are arranged in a left-to-right direction in the display interface, and the tag items are arranged in a top-to-bottom direction in the display interface, and the first touch action is a leftward-rightward sliding operation, and the second touch action is an upward-downward sliding operation.

In another example, the resource items are arranged in a top-to-bottom direction in the display interface, and the tag items are arranged in a left-to-right direction in the display interface, and the first touch action is an upward-downward sliding operation, and the second touch action is a leftward-rightward sliding operation.

According to an aspect, the method also includes detecting a third touch action on the touch control panel; generating a third control instruction corresponding to the third touch action, the third touch action being a clicking operation on the touch control panel; and sending the third control instruction to the VR equipment, the third control instruction being configured to control the VR equipment to select an operation object on the display interface and/or start a selected operation object on the display interface.

Aspects of the disclosure also provide a device for controlling Virtual Reality (VR) equipment. The device includes a processor and a memory configured to store instructions executable by the processor. The processor is configured to detect a touch action on a touch control panel; generate a control instruction corresponding to the touch action, the touch action being a sliding operation along a predetermined direction on the touch control panel; send the control instruction to the VR equipment; detect attributes and arrangements of all operation objects in a current display interface; determine a row number and a column number of all the arranged operation objects; when the row number and the column number of all the arranged operation objects are both larger than 1, control a switching selection to be performed among the operation objects based on the attributes of the operation objects; and when the row number or the column number of all the arranged operation objects is 1, control switching selection to be performed among the operation objects based on an arrangement direction of the operation objects.

Aspects of the disclosure also provide a non-transitory computer-readable storage medium having stored therein instructions that, when executed by a processor, causes the processor to perform a method for controlling Virtual Reality (VR) equipment. The method includes detecting a touch action on a touch control panel; generating a control instruction corresponding to the touch action, the touch action being a sliding operation along a predetermined direction on the touch control panel; sending the control instruction to the VR equipment; detecting attributes and arrangements of all operation objects in a current display interface; determining a row number and a column number of all the arranged operation objects; when the row number and the column number of all the arranged operation objects are both larger than 1, controlling a switching selection to be performed among the operation objects based on the attributes of the operation objects; and when the row number or the column number of all the arranged operation objects is 1, controlling the switching selection to be performed among the operation objects based on an arrangement direction of the operation objects.

It is to be understood that both the foregoing general description and the following detailed description are illustrative and explanatory only and are not restrictive of the present disclosure.

BRIEF DESCRIPTION OF THE DRAWINGS

The accompanying drawings, which are incorporated in and constitute a part of this specification, illustrate aspects consistent with the present disclosure and, together with the description, serve to explain the principles of the present disclosure.

The specific aspects of the present disclosure, which have been illustrated by the accompanying drawings described above, will be described in detail below. These accompanying drawings and description are not intended to limit the scope of the present disclosure in any manner, but to explain the concept of the present disclosure to those skilled in the art via referencing specific aspects.

DETAILED DESCRIPTION

Reference will now be made in detail to exemplary aspects, examples of which are illustrated in the accompanying drawings. The following description refers to the accompanying drawings in which the same numbers in different drawings represent the same or similar elements unless otherwise represented. The implementations set forth in the following description of exemplary aspects do not represent all implementations consistent with the present disclosure. Instead, they are merely examples of apparatuses and methods consistent with aspects related to the present disclosure as recited in the appended claims.

Figure 1:
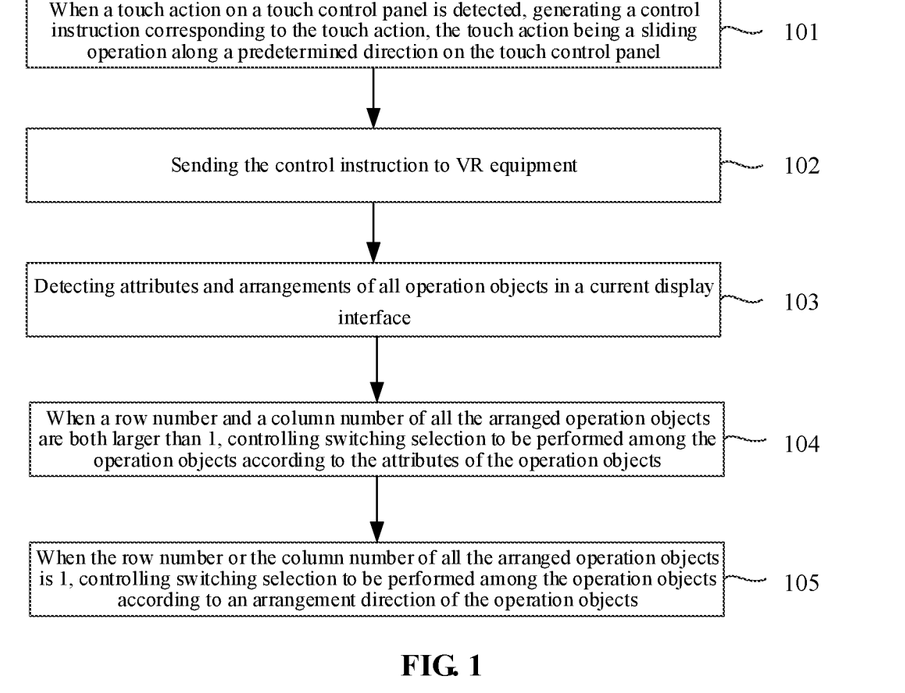
FIG. 1 is a flow chart showing a method for controlling VR equipment, according to an exemplary aspect of the present disclosure.

FIG. 1 is a flow chart showing a method for controlling VR equipment, according to an exemplary aspect. As shown in FIG. 1, the method may include the following steps.

Step 101: when a touch action on a touch control panel is detected, generating a control instruction corresponding to the touch action, the touch action being a sliding operation along a predetermined direction on the touch control panel.

Step 102: sending the control instruction to the VR equipment.

Step 103: detecting attributes and arrangements of all operation objects in a current display interface.

Step 104: when a row number and a column number of all the arranged operation objects are both larger than 1, controlling switching selection to be performed among the operation objects according to the attributes of the operation objects.

Step 105: when the row number or the column number of all the arranged operation objects is 1, controlling the switching selection to be performed among the operation objects according to an arrangement direction of the operation objects.

In the aspect, the Virtual Reality equipment (called as VR equipment for short hereinafter) may include, for example, a VR helmet and VR glasses. The VR equipment may be split VR equipment, and may also be integrated VR equipment, which will not be limited in the aspect. The method for controlling the VR equipment may be executed by control equipment for the VR equipment, such as a handle and a remote controller. A panel configured to identify various touch operations of a user, called as the touch control panel for short, may be arranged on a shell of the control equipment. The user may perform a sliding or clicking operation on the touch control panel of the control equipment to generate a corresponding control instruction. The control equipment sends the control instruction to the VR equipment in a BT or WI-FI manner or the like, thereby controlling various display effects of the VR equipment on the display interface. After receiving the control instruction, the VR equipment may detect the attributes and arrangements of all the operation objects in the current display interface, wherein all the operation objects may include tag items and resource items. It may be determined whether an operation object is a tag item or a resource item according to the attribute of the operation object, wherein the tag item may also be called as a tab item, a page item and the like. The resource item may include, but not limited to, a resource item of a built-in or installed Application (APP) program, or a certain built-in or downloaded runnable resource, link or the like.

Figure 2:
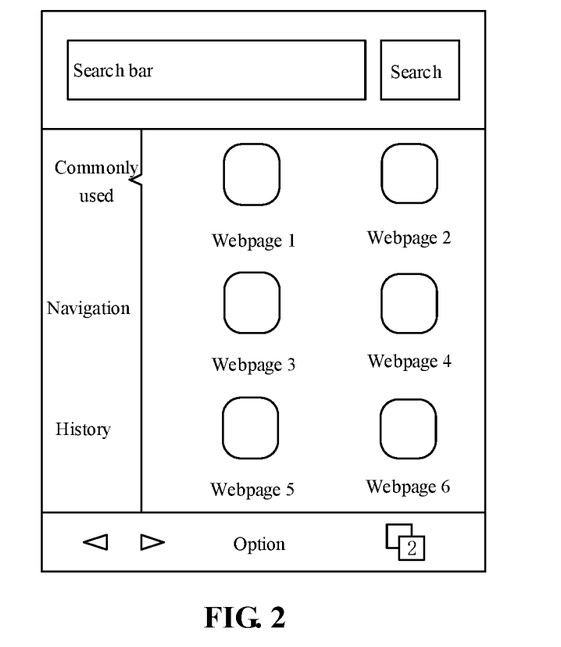
FIG. 2 is an interface diagram of VR equipment, according to an exemplary aspect of the present disclosure.

FIG. 2 is an interface diagram of VR equipment, according to an exemplary aspect. As an example of the aspect, the interface diagram, shown in FIG. 2, of the VR equipment may be an interface diagram corresponding to a web browser, and "commonly used", "navigation" and "history" displayed in the interface may be tag items. When the "commonly used" tag item is selected, "webpage 1" to "webpage 6" displayed in the interface may be resource items (webpage links) under the "commonly used" tag item. If a single clicking or double clicking operation is performed on a webpage link, the VR equipment may display a webpage content corresponding to the webpage link.

Figure 5:
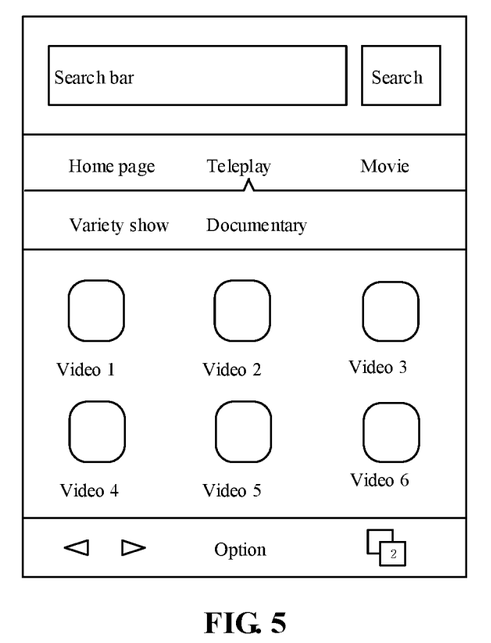
FIG. 5 is another interface diagram of VR equipment, according to an exemplary aspect of the present disclosure.

FIG. 5 is another interface diagram of VR equipment, according to an exemplary aspect. As an example of the aspect, the interface diagram, shown in FIG. 5, of the VR equipment may be an interface diagram corresponding to a video player, and "home page", "teleplay", "movie", "variety show" and "documentary" displayed in the interface may be tag items. When the "teleplay" tag item is selected, "video 1" to "video 6" displayed in the interface may be resource items (video resources) under the "teleplay" tag item. If a single clicking or double clicking operation is performed on a video resource, the VR equipment may play the video resource.

In addition, a corresponding relationship between a sliding operation in a predetermined direction on the touch control panel and an attribute of an operation object may be preset. When all the operation objects include the tag items and the resource items, and the number of rows and columns of all the arranged operation objects are both larger than 1, switching selection is controlled to be performed among different item tags or among the resource items according to the corresponding relationship between the sliding operation in the predetermined direction and the attribute of the operation object.

Figure 3:
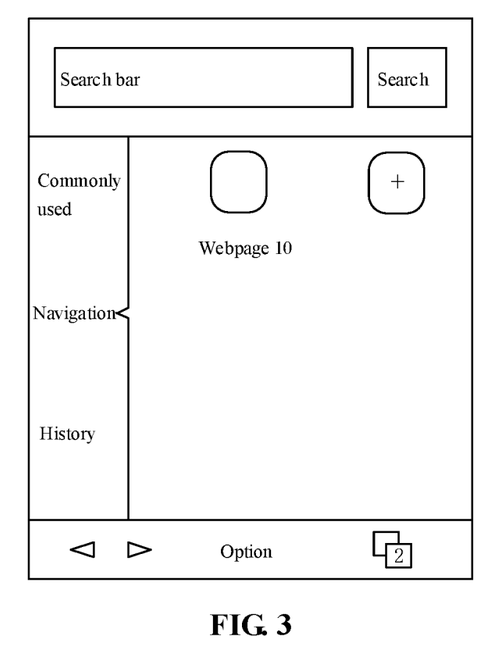
FIG. 3 is another interface diagram of VR equipment, according to an exemplary aspect of the present disclosure.
Figure 4:
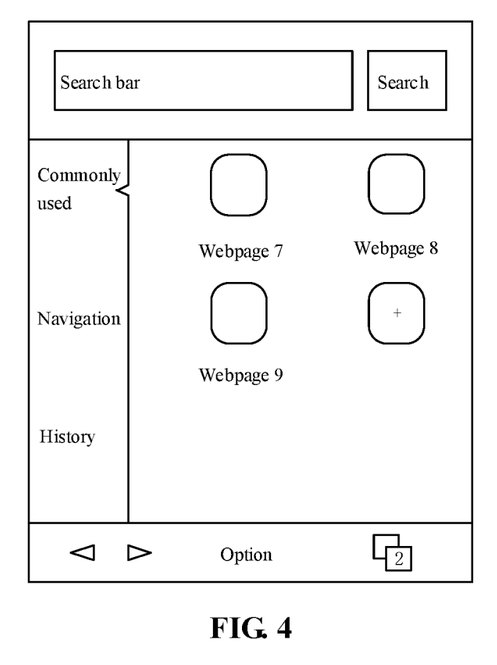
FIG. 4 is another interface diagram of VR equipment, according to an exemplary aspect of the present disclosure.

As an example of the aspect, when the row number or the column number of the arranged operation objects is 1, a control direction of the control equipment for the operation objects of which the row number or the column number is 1 may be set to be an arrangement direction of the operation objects. As shown in FIG. 2, a column number of the tag items is 1, an arrangement direction is a top-bottom direction, and a row number and a column number of the resource items are both larger than 1. Under such a condition, the control equipment may be configured to control switching of the tag items when a touch action of sliding in an upward-downward direction is detected, and control switching (such as line feeding or page turning) of the resource items when a touch action of sliding in a leftward-rightward direction is detected. For example, if the user slides downwards on the touch control panel of the control equipment, as shown in FIG. 2 and FIG. 3, the tag items may be switched from "commonly used" to "navigation". If the user slides leftwards on the touch control panel of the control equipment, as shown in FIG. 2 and FIG. 4, a page turning operation is performed on the resource items (the webpage links).

For example, a first control instruction corresponding to a first touch action is generated when the first touch action on the touch control panel is detected, the first touch action being a sliding operation along a first direction on the touch control panel and the first control instruction being configured to control different resource items in the display interface of the VR equipment to be switched.

For another example, a second control instruction corresponding to a second touch action is generated when the second touch action on the touch control panel is detected, the second touch action being a sliding operation along a second direction on the touch control panel and the second control instruction being configured to control different tag items in the display interface of the VR equipment to be switched.

Wherein, the first direction may usually be different from the second direction. For example, the first direction may be the upward-downward direction, and the second direction may be the leftward-rightward direction. For another example, the first direction may be the leftward-rightward direction, and the second direction may be the upward-downward direction. Implementations for the first direction and the second direction will not be limited in the aspect, and may be flexibly set according to a practical application scenario.

In a possible implementation, different arrangements of the operation objects may also correspond to different touch actions.

For example, the resource items is arranged in a left-right direction in the display interface, and the tag items is arranged in a top-bottom direction in the display interface; and the first touch action is a leftward-rightward sliding operation, and the second touch action is an upward-downward sliding operation.

For another example, the resource items is arranged in a top-bottom direction in the display interface, and the tag items is arranged in a left-right direction in the display interface; and the first touch action is an upward-downward sliding operation, and the second touch action is a leftward-rightward sliding operation.

In a possible implementation, the method may further include:

when a third touch action on the touch control panel is detected, generating a third control instruction corresponding to the third touch action, the third touch action being a clicking operation on the touch control panel; and sending the third control instruction to the VR equipment, the third control instruction being configured to control the VR equipment to select an operation object on the display interface and/or start a selected operation object on the display interface.

Wherein, when different resource items and tag items on the current display interface are switched through the first touch action and the second touch action, if switching to a target operation object (for example, a cursor moves to the target operation object and the operation object is highlighted for display or selected in another form) is implemented, a clicking (for example, single clicking, double clicking or another clicking form) operation may be performed on the touch control panel, thereby confirming that the target operation object is selected or the target operation object is started.

Figure 8:
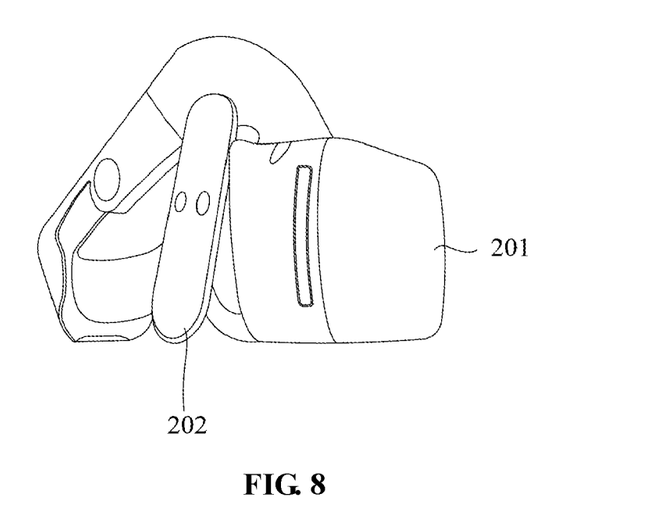
FIG. 8 is a schematic diagram illustrating VR equipment and a handle, according to an exemplary aspect of the present disclosure.

As shown in FIG. 8, for example, the VR equipment is a helmet 201, and the control equipment is a handle 202, wherein the handle 202 may establish a communication connection with the helmet 201 (or a mobile phone in the helmet 201) through BT or WI-FI. The surface of the handle 202 may include a touchpad (or called as a touch control panel). A control instruction may be generated by sliding on the touchpad. The handle 202 sends the control instruction to the helmet 201 (or another intelligent terminal such as the mobile phone in the helmet 201), thereby controlling an APP run in the helmet 201 (or the other intelligent terminal such as the mobile phone in the helmet 201).

Wherein, if the VR equipment is an all-in-one machine, it is unnecessary to arrange the other intelligent terminal such as the mobile phone therein. If the VR equipment is not an all-in-one machine, the other intelligent terminal such as the mobile phone may be arranged in the helmet 201, and the APP is run in the other intelligent terminal such as the mobile phone.

Some examples of controlling the VR equipment through the handle 202 will be given below.

A first example: a current interface displayed by the APP running in the VR equipment includes both tab items (or called as tag items) and APP items (or video resource items and the like), and the two items are distributed in different directions. A page turning function may be realized by a leftward-rightward sliding operation on the touchpad of the handle 202, and different APP items are switched during page turning. A tab switching function may also be realized by an upward-downward sliding operation on the touchpad of the handle, and vice versa.

A second example: a sliding direction of the display interface of the APP corresponding to a sliding operation of the handle 202 is determined according to the arrangement of the resource items. For example, if the resource items in the interface are arranged in a 1*n manner, page turning and switching of the resource items in the display interface of the APP may be realized on the touchpad through the upward-downward sliding operation, as an example of the aspect.

A third example: a currently selected object such as an APP, a video to be played and a link may be displayed on the display interface by highlighting or another special effect. If an operation of the user, such a single clicking operation and a double clicking operation, is detected on the touchpad of the handle 202, an instruction may be sent to the helmet 201. After receiving the instruction, the helmet 201 may run or load the selected object on the display interface.

Figure 6:
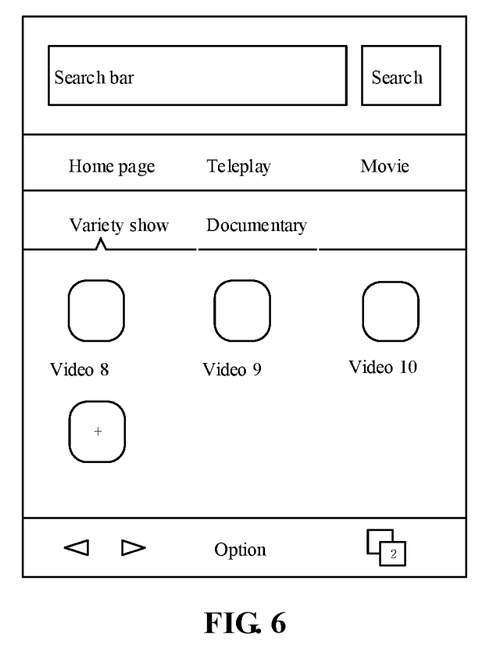
FIG. 6 is another interface diagram of VR equipment, according to an exemplary aspect of the present disclosure.
Figure 7:
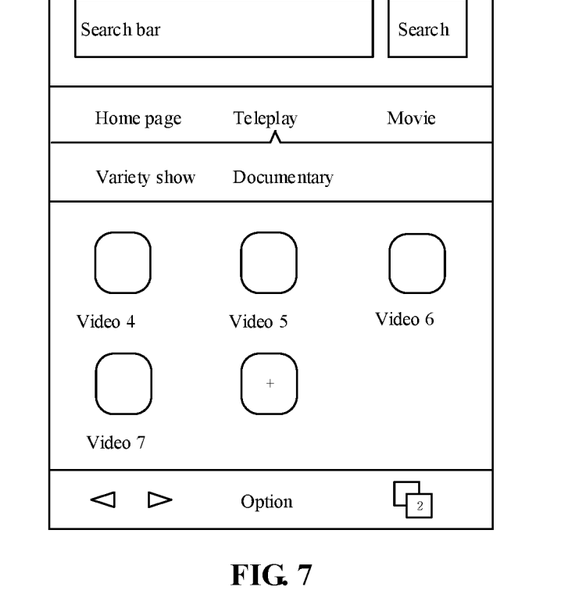
FIG. 7 is another interface diagram of VR equipment, according to an exemplary aspect of the present disclosure.

As an example of the aspect, under the condition that the row number and the column number of the arranged operation objects are both larger than 1, a control direction in which the control equipment controls the operation objects with a certain attribute may be set to be a preset direction. As shown in FIG. 5, the row number and the column number of the tag items are both larger than 1, and the row number and the column number of the resource items are also both larger than 1. Under such a condition, the control equipment may be configured to control switching of the tag items when the touch action of sliding in the leftward-rightward direction is detected, and control switching (such as line feeding or page turning) of the resource items when the touch action of sliding in the upward-downward direction is detected. For example, if the user slides rightwards on the touch control panel of the control equipment, as shown in FIG. 5 and FIG. 6, the tag items may be switched from "teleplay" to "variety show". If the user slides upwards on the touch control panel of the control equipment, as shown in FIG. 5 and FIG. 7, a line feeding operation is performed on the resource items (video resources).

According to the method for controlling the VR helmet 201 in the present disclosure, when it is detected the touch action of sliding along the predetermined direction on the touch control panel, the control instruction corresponding to the touch action may be generated, and the VR equipment may be controlled according to the control instruction to control switching selection to be performed among operation objects on the display interface according to the attributes and arrangements of the operation objects, so that an operation over the display interface of the VR equipment is simplified, and the VR equipment may be controlled more conveniently and rapidly.

For example, a corresponding control instruction is generated in the handle 202 through a sliding operation and page layout of the touchpad. It is unnecessary to provide sliding and page turning control buttons for page turning and tab switching on the display interface of the helmet 201, and the touchpad on the handle 202 may be directly slid for control, so that the operation is simplified.

According to the method for controlling the VR equipment in the present disclosure, when the touch action of sliding along the predetermined direction on the touch control panel is detected, the control instruction corresponding to the touch action may be generated, and the VR equipment may be controlled according to the control instruction to control switching selection to be performed among the operation objects on the display interface according to the attributes and arrangements of the operation objects, so that the operation over the display interface of the VR equipment is simplified, and the VR equipment may be controlled more conveniently and rapidly.

Figure 9:
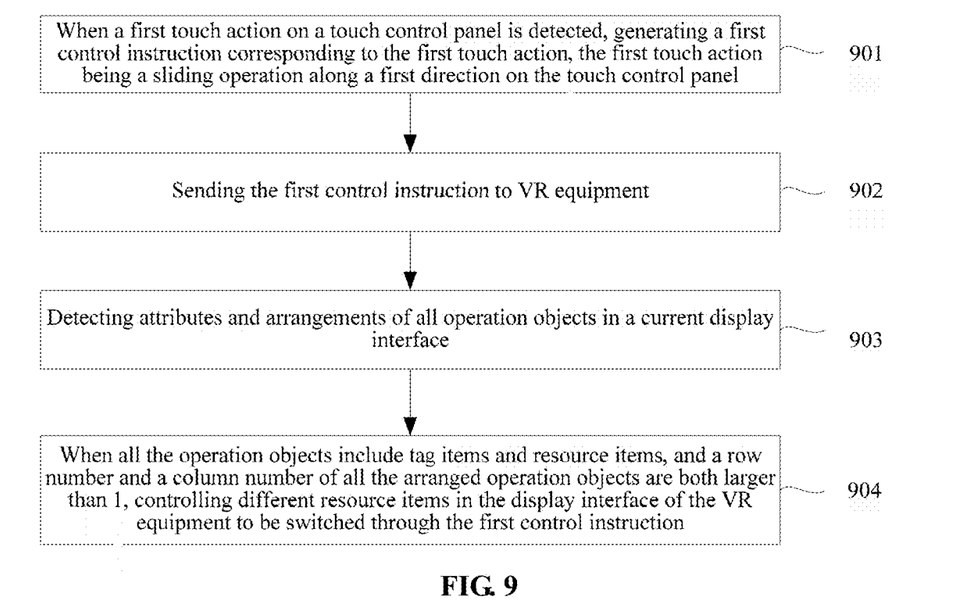
FIG. 9 is a flow chart showing a method for controlling VR equipment, according to an exemplary aspect of the present disclosure.

FIG. 9 is a flow chart showing a method for controlling VR equipment, according to an exemplary aspect. As shown in FIG. 9, the method may include the following steps.

Step 901: when a first touch action on a touch control panel is detected, generating a first control instruction corresponding to the first touch action, the first touch action being a sliding operation along a first direction on the touch control panel.

Step 902: sending the first control instruction to the VR equipment.

Step 903: detecting attributes and arrangements of all operation objects in a current display interface.

Step 904: when all the operation objects include tag items and resource items, and a row number and a column number of all the arranged operation objects are both larger than 1, controlling different resource items in the display interface of the VR equipment to be switched through the first control instruction.

As an example of the aspect, the first direction may be an upward-downward direction or a leftward-rightward direction. The direction of the first touch action may be determined according to a starting position and an ending position of the first touch action. As shown in FIG. 5, the operation objects include the tag items (such as "home page", "teleplay", "movie", "variety show" and "documentary") and resource items (such as video 1 to video 10), a row number and a column number of the tag items are both larger than 1, and a row number and a column number of the resource items are also both larger than 1. Under such a condition, if the first direction is set to be the upward-downward direction, different resource items in the display interface of the VR equipment are controlled to be switched when the first touch action of sliding in the upward-rightward direction is detected. For example, if a user slides upwards on the touch control panel, as shown in FIG. 5 and FIG. 7, a line feeding operation is performed on the resource items (video resources).

Figure 10:
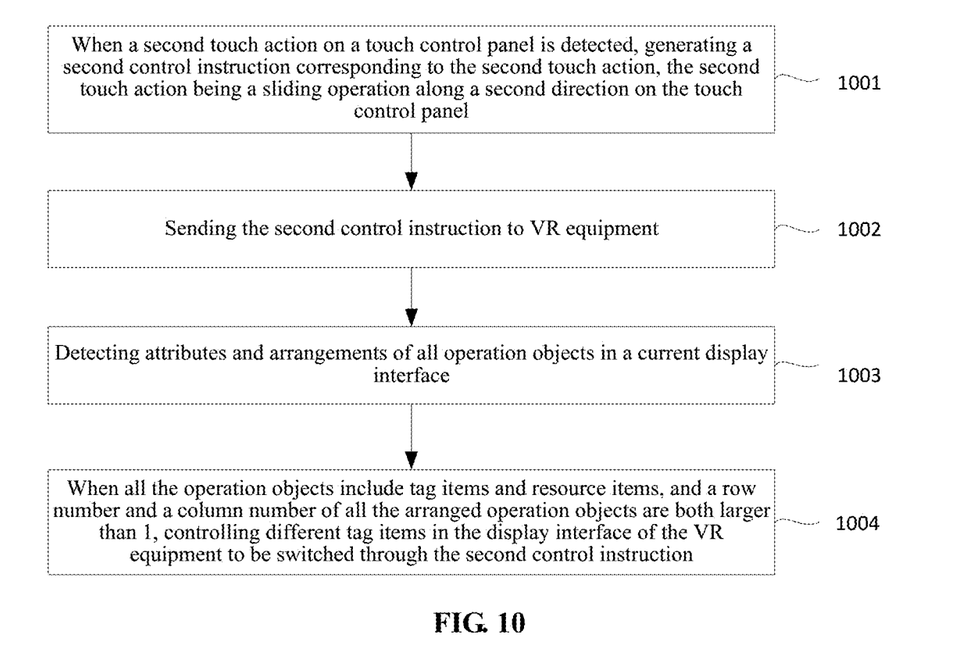
FIG. 10 is a flow chart showing a method for controlling VR equipment, according to an exemplary aspect of the present disclosure.

FIG. 10 is a flow chart showing a method for controlling VR equipment, according to an exemplary aspect. As shown in FIG. 10, the method may include the following steps.

Step 1001: when a second touch action on a touch control panel is detected, generating a second control instruction corresponding to the second touch action, the second touch action being a sliding operation along a second direction on the touch control panel.

Step 1002: sending the second control instruction to the VR equipment.

Step 1003: detecting attributes and arrangements of all operation objects in a current display interface.

Step 1004: when all the operation objects include tag items and resource items, and a row number and a column number of all the arranged operation objects are both larger than 1, controlling different resource items in the display interface of the VR equipment to be switched through the second control instruction.

As an example of the aspect, the second direction is different from the first direction. When the first direction is an upward-downward direction, the second direction may be a leftward-rightward direction. When the first direction is the leftward-rightward direction, the second direction may be the upward-downward direction. The direction of the second touch action may be determined according to a starting position and an ending position of the second touch action. As shown in FIG. 5, the operation objects include the tag items (such as "home page", "teleplay", "movie", "variety show" and "documentary") and resource items (such as video 1 to video 10), a row number and a column number of the tag items are both larger than 1, and a row number and a column number of the resource items are also both larger than 1. Under such a condition, if the second direction is set to be the leftward-rightward direction, different tag items in the display interface of the VR equipment are controlled to be switched when the second touch action of sliding in the leftward-rightward direction is detected. For example, if a user slides rightwards on the touch control panel, as shown in FIG. 5 and FIG. 6, the tag items may be switched from "teleplay" to "variety show".

Figure 11:
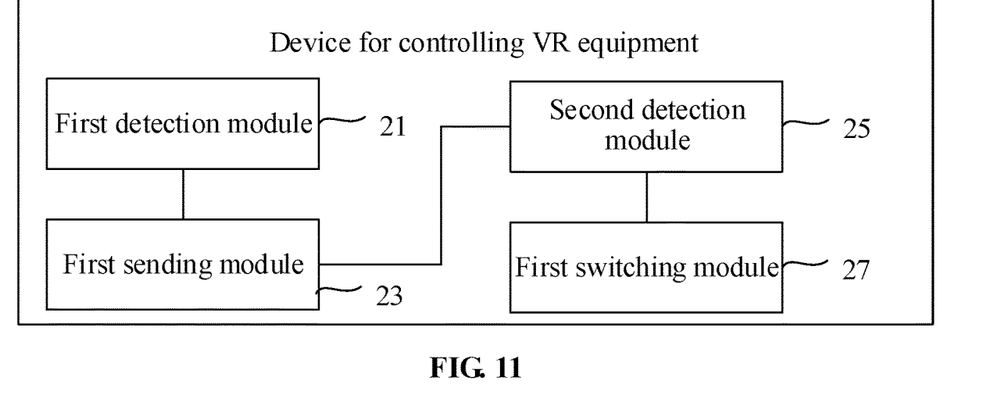
FIG. 11 is a block diagram of a device for controlling VR equipment, according to an exemplary aspect of the present disclosure.

FIG. 11 is a block diagram of a device for controlling VR equipment, according to an exemplary aspect. As shown in FIG. 11, the device may include a first detection module 21, a first sending module 23, a second detection module 25 and a first switching module 27.

Wherein, the first detection module 21 is configured to, when a touch action on a touch control panel is detected, generate a control instruction corresponding to the touch action, the touch action being a sliding operation along a predetermined direction on the touch control panel;

the first sending module 23 is configured to send the control instruction to the VR equipment;

the second detection module 25 is configured to detect attributes and arrangements of all operation objects in a current display interface; and the first switching module 27 is configured to, when a row number and a column number of all the arranged operation objects are both larger than 1, control switching selection to be performed among the operation objects according to the attributes of the operation objects, and when the row number or the column number of all the arranged operation objects is 1, control switching selection to be performed among the operation objects according to an arrangement direction of the operation objects.

According to the device for controlling the VR equipment in the present disclosure, when the touch action of sliding along the predetermined direction on the touch control panel is detected, the control instruction corresponding to the touch action may be generated, and the VR equipment may be controlled according to the control instruction to control switching selection to be performed among the operation objects on the display interface according to the attributes and arrangements of the operation objects, so that an operation over the display interface of the VR equipment is simplified, and the VR equipment may be controlled more conveniently and rapidly.

Figure 12:
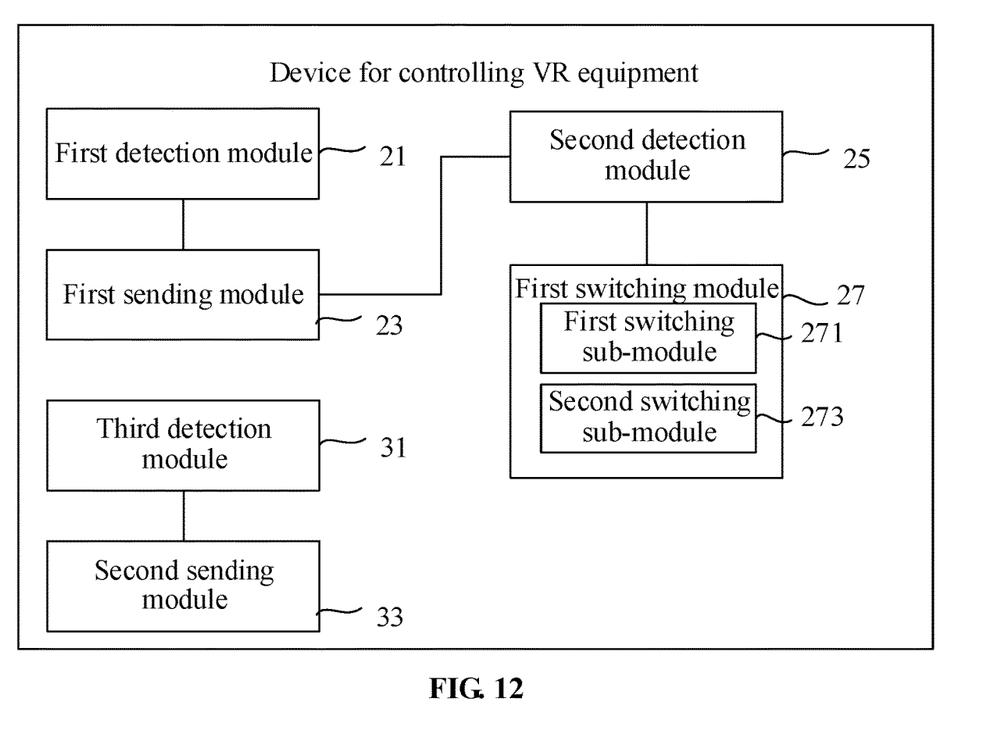
FIG. 12 is a block diagram of a device for controlling VR equipment, according to another exemplary aspect of the present disclosure.

FIG. 12 is a block diagram of a device for controlling VR equipment, according to another exemplary aspect. Components with the same reference signs in FIG. 12 and FIG. 11 have the same meanings, and will not be elaborated herein.

As shown in FIG. 12, a main difference from the previous aspect is that the first switching module is further configured to, when all the operation objects include tag items and resource items, and the row number and the column number of all the arranged operation objects are both larger than 1, control switching selection to be performed among different tag items or among the resource items according to a corresponding relationship between a sliding operation in a predetermined direction and an attribute of an operation object.

In a possible implementation, the first switching module 27 includes:

a first switching sub-module 271, configured to generate a first control instruction corresponding to a first touch action when the first touch action on the touch control panel is detected, the first touch action being a sliding operation along a first direction on the touch control panel and the first control instruction being configured to control different resource items in the display interface of the VR equipment to be switched; and a second switching sub-module 273, configured to generate a second control instruction corresponding to a second touch action when the second touch action on the touch control panel is detected, the second touch action being a sliding operation along a second direction on the touch control panel and the second control instruction being configured to control different tag items in the display interface of the VR equipment to be switched, wherein the first direction is different from the second direction.

In a possible implementation, the resource items is are arranged in a left-right direction in the display interface, and the tag items is are arranged in a top-bottom direction in the display interface; and the first touch action is a leftward-rightward sliding operation, and the second touch action is an upward-downward sliding operation.

In a possible implementation, the resource items is are arranged in a top-bottom direction in the display interface, and the tag items is are arranged in a left-right direction in the display interface; and the first touch action is an upward-downward sliding operation, and the second touch action is a leftward-rightward sliding operation.

In a possible implementation, the device for controlling the VR equipment further includes:

a third detection module 31, configured to, when a third touch action on the touch control panel is detected, generate a third control instruction corresponding to the third touch action, the third touch action being a clicking operation on the touch control panel; and a second sending module 33, configured to send the third control instruction to the VR equipment, the third control instruction being configured to control the VR equipment to select an operation object on the display interface and/or start a selected operation object on the display interface.

According to the device for controlling the VR equipment in the present disclosure, when the touch action of sliding along the predetermined direction on the touch control panel is detected, the control instruction corresponding to the touch action may be generated, and the VR equipment may be controlled through the control instruction to control switching selection to be performed among the operation objects on the display interface according to the attributes and arrangements of the operation objects, so that an operation over the display interface of the VR equipment is simplified, and the VR equipment may be controlled more conveniently and rapidly.

With respect to the devices in the above aspects, the specific manners for performing operations for individual modules therein have been described in detail in the aspects regarding the methods, which will not be elaborated herein.

Figure 13:
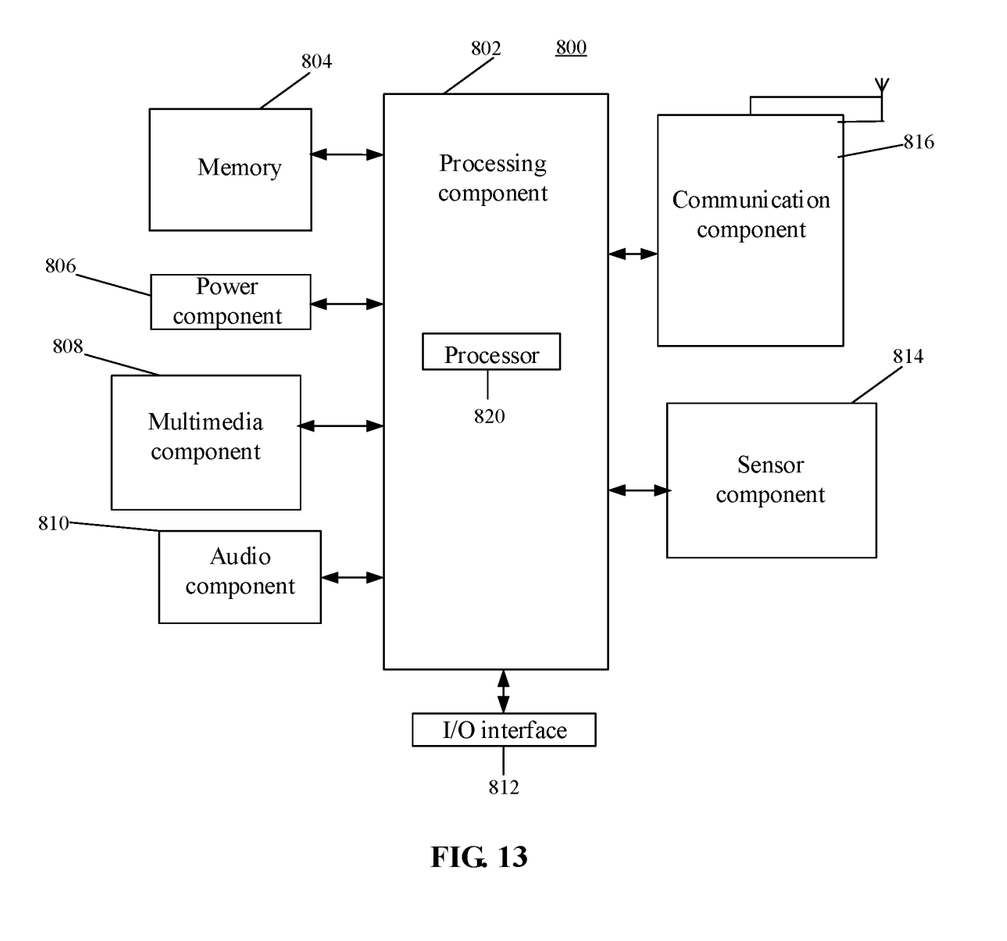
FIG. 13 is a block diagram of a device for controlling VR equipment, according to another exemplary aspect of the present disclosure.

FIG. 13 is a block diagram of a device 800 for controlling VR equipment, according to an exemplary aspect. For example, the device 800 may be a mobile phone, a computer, a digital broadcast terminal, a messaging device, a gaming console, a tablet, a medical device, exercise equipment, a personal digital assistant and the like.

Referring to FIG. 13, the device 800 may include one or more of the following components: a processing component 802, a memory 804, a power component 806, a multimedia component 808, an audio component 810, an Input/Output (I/O) interface 812, a sensor component 814, and a communication component 816.

The processing component 802 typically controls overall operations of the device 800, such as the operations associated with display, telephone calls, data communications, camera operations, and recording operations. The processing component 802 may include one or more processors 820 to execute instructions to perform all or part of the steps in the abovementioned method. Moreover, the processing component 802 may include one or more modules which facilitate interaction between the processing component 802 and the other components. For instance, the processing component 802 may include a multimedia module to facilitate interaction between the multimedia component 808 and the processing component 802.

The memory 804 is configured to store various types of data to support the operation of the device 800. Examples of such data include instructions for any APP programs or methods operated on the device 800, contact data, phonebook data, messages, pictures, video, etc. The memory 804 may be implemented by any type of volatile or non-volatile memory devices, or a combination thereof, such as a Static Random Access Memory (SRAM), an Electrically Erasable Programmable Read-Only Memory (EEPROM), an Erasable Programmable Read-Only Memory (EPROM), a Programmable Read-Only Memory (PROM), a Read-Only Memory (ROM), a magnetic memory, a flash memory, and a magnetic or optical disk.

The power component 806 provides power for various components of the device 800. The power component 806 may include a power management system, one or more power supplies, and other components associated with the generation, management and distribution of power for the device 800.

The multimedia component 808 includes a screen providing an output interface between the device 800 and a user. In some aspects, the screen may include a Liquid Crystal Display (LCD) and a Touch Panel (TP). If the screen includes the TP, the screen may be implemented as a touch screen to receive an input signal from the user. The TP includes one or more touch sensors to sense touches, swipes and gestures on the TP. The touch sensors may not only sense a boundary of a touch or swipe action, but also detect a duration and pressure associated with the touch or swipe action. In some aspects, the multimedia component 808 includes a front camera and/or a rear camera. The front camera and/or the rear camera may receive external multimedia data when the device 800 is in an operation mode, such as a photographing mode or a video mode. Each of the front camera and the rear camera may be a fixed optical lens system or have focusing and optical zooming capabilities.

The audio component 810 is configured to output and/or input an audio signal. For example, the audio component 810 includes a Microphone (MIC), and the MIC is configured to receive an external audio signal when the device 800 is in the operation mode, such as a call mode, a recording mode and a voice recognition mode. The received audio signal may be further stored in the memory 804 or sent through the communication component 816. In some aspects, the audio component 810 further includes a speaker configured to output the audio signal.

The I/O interface 812 provides an interface between the processing component 802 and a peripheral interface module, and the peripheral interface module may be a keyboard, a click wheel, a button and the like. The button may include, but not limited to: a home button, a volume button, a starting button and a locking button.

The sensor component 814 includes one or more sensors configured to provide status assessment in various aspects for the device 800. For instance, the sensor component 814 may detect an on/off status of the device 800 and relative positioning of components, such as a display and small keyboard of the device 800, and the sensor component 814 may further detect a change in a position of the device 800 or a component of the device 800, presence or absence of contact between the user and the device 800, orientation or acceleration/deceleration of the device 800 and a change in temperature of the device 800. The sensor component 814 may include a proximity sensor configured to detect presence of an object nearby without any physical contact. The sensor component 814 may also include a light sensor, such as a Complementary Metal Oxide Semiconductor (CMOS) or Charge Coupled Device (CCD) image sensor, configured for use in an imaging application. In some aspects, the sensor component 814 may also include an acceleration sensor, a gyroscope sensor, a magnetic sensor, a pressure sensor or a temperature sensor.

The communication component 816 is configured to facilitate wired or wireless communication between the device 800 and other equipment. The device 800 may access a communication-standard-based wireless network, such as a WI-FI network, a 2nd-Generation (2G) or 3rd-Generation (3G) network or a combination thereof. In an exemplary aspect, the communication component 816 receives a broadcast signal or broadcast associated information from an external broadcast management system through a broadcast channel. In an exemplary aspect, the communication component 816 further includes a Near Field Communication (NFC) module to facilitate short-range communication. For example, the NFC module may be implemented on the basis of a Radio Frequency Identification (RFID) technology, an Infrared Data Association (IrDA) technology, an Ultra-WideBand (UWB) technology, a BT technology and another technology.

In an exemplary aspect, the device 800 may be implemented by one or more Application Specific Integrated Circuits (ASICs), Digital Signal Processors (DSPs), Digital Signal Processing Devices (DSPDs), Programmable Logic Devices (PLDs), Field Programmable Gate Arrays (FPGAs), controllers, micro-controllers, microprocessors or other electronic components, and is configured to execute the abovementioned method.

In an exemplary aspect, there is also provided a non-transitory computer-readable storage medium including an instruction, such as the memory 804 including an instruction, and the instruction may be executed by the processor 820 of the device 800 to implement the abovementioned method. For example, the non-transitory computer-readable storage medium may be a ROM, a Random Access Memory (RAM), a Compact Disc Read-Only Memory (CD-ROM), a magnetic tape, a floppy disc, optical data storage equipment and the like.

It is noted that the various modules, sub-modules, units, and components in the present disclosure can be implemented using any suitable technology. For example, a module may be implemented using circuitry, such as an integrated circuit (IC). As another example, a module may be implemented as a processing circuit executing software instructions.

Other aspects of the present disclosure will be apparent to those skilled in the art from consideration of the specification and practice of the present disclosure. This application is intended to cover any variations, uses, or adaptations of the present disclosure following the general principles thereof and including such departures from the present disclosure as come within known or customary practice in the art. It is intended that the specification and examples be considered as exemplary only, with a true scope and spirit of the present disclosure being indicated by the following claims.

It will be appreciated that the present disclosure is not limited to the exact construction that has been described above and illustrated in the accompanying drawings, and that various modifications and changes may be made without departing from the scope thereof. It is intended that the scope of the present disclosure only be limited by the appended claims.

What is claimed is:

1. A method for controlling Virtual Reality (VR) equipment, comprising:
   detecting a touch action on a touch control panel;
   generating a control instruction corresponding to the touch action, the touch action being a sliding operation along a predetermined direction on the touch control panel;
   sending the control instruction to the VR equipment;
   receiving types and arrangements of all operation objects in a current display interface of the VR equipment, detected by the VR equipment in response to that the control instruction is received, wherein the types of all the operation objects comprise tag items and resource items;
   determining a row number and a column number of all the arranged operation objects;
   when the row number and the column number of all the arranged operation objects are both larger than 1, controlling a switching selection to be performed among different tag items or among different resource items based on a corresponding relationship between the sliding operation in the predetermined direction and a type of an operation object; and
   when the row number or the column number of all the arranged operation objects is 1, controlling a switching selection to be performed among different tag items or among different resource items based on a corresponding relationship between the sliding operation in predetermined direction and an arrangement direction of the tag items or the resource items, wherein the arrangement direction of the tag items or the resource items comprises an arrangement in a top-bottom direction in the display interface or an arrangement in a left-right direction in the display interface.

2. The method of claim 1, further comprising:
   detecting a first touch action on the touch control panel;
   generating a first control instruction corresponding to the first touch action, the first touch action being a sliding operation along a first direction on the touch control panel, and the first control instruction being configured to control different resource items in the display interface of the VR equipment to be switched;
   detecting a second touch action on the touch control panel; and
   generating a second control instruction corresponding to the second touch action, the second touch action being a sliding operation along a second direction on the touch control panel, and the second control instruction being configured to control different tag items in the display interface of the VR equipment to be switched,
   wherein the first direction is different from the second direction.

3. The method of claim 2, wherein the resource items are arranged in a left-to-right direction in the display interface, and the tag items are arranged in a top-to-bottom direction in the display interface, and
   wherein the first touch action is a leftward-rightward sliding operation, and the second touch action is an upward-downward sliding operation.

4. The method of claim 2, wherein the resource items are arranged in a top-to-bottom direction in the display interface, and the tag items are arranged in a left-to-right direction in the display interface, and
   wherein the first touch action is an upward-downward sliding operation, and the second touch action is a leftward-rightward sliding operation.

5. The method of claim 2, further comprising:
   detecting a third touch action on the touch control panel;
   generating a third control instruction corresponding to the third touch action, the third touch action being a clicking operation on the touch control panel; and
   sending the third control instruction to the VR equipment, the third control instruction being configured to control the VR equipment to select an operation object on the display interface and/or start a selected operation object on the display interface.

6. A device for controlling Virtual Reality (VR) equipment, comprising:
   a processor; and
   a memory configured to store instructions executable by the processor,
   wherein the processor is configured to:
      detect a touch action on a touch control panel;
      generate a control instruction corresponding to the touch action, the touch action being a sliding operation along a predetermined direction on the touch control panel;
      send the control instruction to the VR equipment;
      receive types and arrangements of all operation objects in a current display interface of the VR equipment, detected by the VR equipment in response to that the control instruction is received, wherein the types of all the operation objects comprise tag items and resource items;
      determine a row number and a column number of all the arranged operation objects;
      when the row number and the column number of all the arranged operation objects are both larger than 1, control a switching selection to be performed among different tag items or among different resource items based on a corresponding relationship between the sliding operation in predetermined direction and a type of an operation object; and when the row number or the column number of all the arranged operation objects is 1, control a switching selection to be performed among different tag items or among different resource items based on a corresponding relationship between the sliding operation in predetermined direction and an arrangement direction of the tag items or the resource items, wherein the arrangement direction of the tag items or the resource items comprises an arrangement in a top-bottom direction in the display interface or an arrangement in a left-right direction in the display interface.

7. The device of claim 6, wherein the processor is further configured to:

detect a first touch action on the touch control panel;

generate a first control instruction corresponding to the first touch action, the first touch action being a sliding operation along a first direction on the touch control panel, and the first control instruction being configured to control different resource items in the display interface of the VR equipment to be switched;

detect a second touch action on the touch control panel; and generate a second control instruction corresponding to the second touch action, the second touch action being a sliding operation along a second direction on the touch control panel, and the second control instruction being configured to control different tag items in the display interface of the VR equipment to be switched, wherein the first direction is different from the second direction.

8. The device of claim 7, wherein the resource items are arranged in a left-to-right direction in the display interface, and the tag items are arranged in a top-to-bottom direction in the display interface, and wherein the first touch action is a leftward-rightward sliding operation, and the second touch action is an upward-downward sliding operation.

9. The device of claim 7, wherein the resource items are arranged in a top-to-bottom direction in the display interface, and the tag items are arranged in a left-to-right direction in the display interface, and wherein the first touch action is an upward-downward sliding operation, and the second touch action is a leftward-rightward sliding operation.

10. The device of claim 6, wherein the processor is further configured to:

detect a third touch action on the touch control panel;

generate a third control instruction corresponding to the third touch action, the third touch action being a clicking operation on the touch control panel; and send the third control instruction to the VR equipment, the third control instruction being configured to control the VR equipment to select an operation object on the display interface and/or start a selected operation object on the display interface.

11. A non-transitory computer-readable storage medium having stored therein instructions that, when executed by a processor, causes the processor to perform a method for controlling Virtual Reality (VR) equipment, the method comprising:

detecting a touch action on a touch control panel;

generating a control instruction corresponding to the touch action, the touch action being a sliding operation along a predetermined direction on the touch control panel;

sending the control instruction to the VR equipment;

receiving types and arrangements of all operation objects in a current display interface of the VR equipment, detected by the VR equipment in response to that the control instruction is received, wherein the types of all the operation objects comprise tag items and resource items;

determining a row number and a column number of all the arranged operation objects;

when the row number and the column number of all the arranged operation objects are both larger than 1, controlling a switching selection to be performed among different tag items or among different resource items based on a corresponding relationship between the sliding operation in the predetermined direction and a type of an operation object; and when the row number or the column number of all the arranged operation objects is 1, controlling a switching selection to be performed among different tag items or among different resource items based on a corresponding relationship between the sliding operation in predetermined direction and an arrangement direction of the tag items or the resource items, wherein the arrangement direction of the tag items or the resource items comprises an arrangement in a top-bottom direction in the display interface or an arrangement in a left-right direction in the display interface.

* * * * *